United States Patent [19]

Katano et al.

[11] Patent Number: 4,485,235
[45] Date of Patent: Nov. 27, 1984

[54] PROCESS FOR PREPARING 7-α-METHOXYCEPHEM COMPOUNDS

[75] Inventors: Kiyoaki Katano; Kunio Atsumi, both of Yokohama; Fumio Kai, Fujisawa; Ken Nishihata; Eiichi Akita, both of Yokohama, all of Japan

[73] Assignee: Meiji Seika Kaisha Ltd., Tokyo, Japan

[21] Appl. No.: 373,700

[22] Filed: Apr. 30, 1982

[30] Foreign Application Priority Data

May 14, 1981 [JP] Japan ................................. 56-71343

[51] Int. Cl.³ ................. C07D 501/57; A61K 31/545
[52] U.S. Cl. .................................... 544/021; 424/246; 544/26
[58] Field of Search ........................... 544/21, 26, 27; 424/246

[56] References Cited

U.S. PATENT DOCUMENTS 4,162,251  7/1979  Hiraoka et al. ..................... 544/21
4,229,573 10/1980  Shibuya et al. ..................... 544/21

OTHER PUBLICATIONS

Diagram—Present Invention & Hiraoka et al., Journal of the American Chemical Society, vol. 99, pp. 505–507, (1977).
J. Org. Chem., vol. 38, No. 5, pp. 943–950, (1973).
Tetrahedron Letters No. 31, pp. 2705–2708, (1975).
Tetrahedron Letters No. 16, pp. 1307–1310, (1976).
Journal of the American Chemical Society, 95:7, pp. 2401–2403, (1973).
Journal of the American Chemical Society, 99:16, pp. 5505–5507, (1977).
Journal of the American Chemical Society, 94:4, pp. 1408–1410, (1972).

Primary Examiner—Nicholas S. Rizzo
Attorney, Agent, or Firm—Schwartz, Jeffery, Schwaab, Mack, Blumenthal & Koch

[57] ABSTRACT

Disclosed is a novel cephem compound represented by the formula:

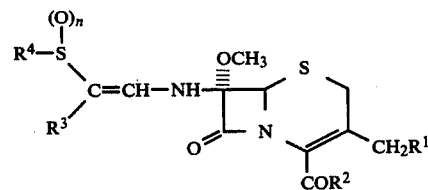

wherein $R^1$, $R^2$, $R^3$, $R^4$ and n are as defined in the specification, which is a useful intermediate for synthesizing various cephalosporin antibiotics having a methoxy group at the 7α-position thereof. Also disclosed is a process for preparing the same.

3 Claims, No Drawings

PROCESS FOR PREPARING 7-α-METHOXYCEPHEM COMPOUNDS

BACKGROUND OF THE INVENTION

This invention relates to a new class of cephem derivatives and a process for preparing the same. More particularly, it relates to a cephem compound which is a new synthetic intermediate useful for various cephalosporin antibiotics having a methoxy group at the 7α-position thereof and a new process for preparing the said cephem compound. Still more particularly, this invention can provide a cephem compound having a methoxy group at the 7α-position thereof and a new process for introducing a methoxy group into a cephalosporin moiety at the 7α-position thereof.

As a group of cephalosporin-type antibiotic substances having a methoxy group at the 7α-position thereof, cephamycin-type antibiotics have been found to be naturally present and they have also been found to exhibit an excellent antibiotic activity by reason of the characteristic chemical structure of having a methoxy group at the 7α-position thereof. Since then, there have been synthesized many 7α-methoxycephalosporin derivatives. On the other hand, various studies have been made on a new process for chemically introducing a methoxy group into a cephem ring at the 7α-position thereof.

Some of these new derivatives have already been given with an established evaluation as an excellent antibiotic substance and practically applied as a chemotherapeutic agent for clinical use. Accordingly, a chemical process for introducing a methoxy group into a cephalosporin skeleton at the 7α-position thereof has been regarded as being commercially of utmost importance and there have hitherto been proposed various processes therefor. Illustrative examples thereof may include the following processes:

(1) The process, namely acylimine process, wherein a 7(or 6)-acylaminocephalosporin (or penicillin) is reacted with a positive halogen compound such as tert-butylhypochlorite in the presence of a strong base to form the corresponding acylimino compound followed by addition of methanol to the so formed compound (J. Am. Chem. Soc., 95 2401 (1973)).

(2) The process, namely carbanion process, wherein the amino group at the 7(or 6)-position is converted to Schiff base, the corresponding carbanion at the 7(or 6)-position is formed from the Schiff base by the action of a strong base, the said carbanion is reacted with a methanethiosulfonate or a positive halogen compound to form a 7α(or 6α)-methylthio- or halo derivative and then the latter derivative is converted to the corresponding 7α(or 6α)-methoxy derivative with methanol (J. Org. Chem., 38, 943 (1973)).

(3) The methoxy-introducing process wherein the Schiff base of the 7(or 6)-amino group with 3,5-di-tert-butyl-4-hydroxybenzaldehyde is oxidized to the quinoneimine form and then methanol is added to the said imine form (Tetrahedron Letters., 1975, 2705).

(4) The process wherein an α-halo- or α,α-dihaloacetamidocephalosporin (or penicillin) or the vinylog thereof is converted to the corresponding iminohalogenated form, the imino ether is derived from the latter form by the substitution of the halogen with methanol, the said imino ether is converted to the corresponding vinyl imine by a 1,4-dehydrohalogenation reaction with a strong base and 1,4-addition of methanol to the said vinyl imine is conducted to introduce a methoxy group at the 7α(or 6α)-position thereof (Tetrahedron Letters., 1976, 1307).

(5) The process wherein a 7(or 6)-sulfenamidocephalosporin (or penicillin) is oxidized to the corresponding sulfenimine derivative and methanol is added to the said derivative (J. Am. Chem. Soc. 99, 5505 (1977)).

(6) The process comprising diazotization of the 7(or 6)-amino group and subsequent addition reaction of an azide compound, e.g., a halogen azide to the diazo form (J. Am. Chem. Soc., 94, 1408 (1972)).

However, the above-recited processes are not always said to be complete without any defaults and it is the present situation that there have been made continuous studies on a variety of new or improved processes for a industrially satisfactory process.

For instance, the above processes have the following defects or difficulties and hence there has been desired a development of a far more excellent process.

The above process (1) has a defect that oxidized by-products tend to be produced owing to the strong oxidizing agent employed if there is present a side-chain liable to be oxidized, in particular, a side-chain containing a sulfide bond. The above processes (1), (2) and (4) involve difficult points that a specific reaction condition such as an extremely low temperature for the reaction (namely, −78° C.) should be required and a strong base, such as lithium methoxide and the like should be employed, which may readily cause a β-lactam ring cleavage. The above processes (3) and (5) involve heterogenous reaction employing a large excess of a metal oxide (namely, a solid phase), but the processes show such a difficult point that it is difficult to control such heterogenous reaction if practised in an industrial scale. The above process (6) shows such defects that addition of the azide compound is not stereo-selective with a yield being poor, that long and complicated reaction pathway is needed and so on.

SUMMARY OF THE INVENTION

The present inventors have made extensive studies for a new methoxylation reaction which may be practised under a mild reaction condition by way of simple reaction procedures with high selectivity and efficiency and, as a result, have found out a new process involving a novel 7α-methoxylation reaction and new 7α-methoxycephem compounds, as illustrated by the following reaction equation:

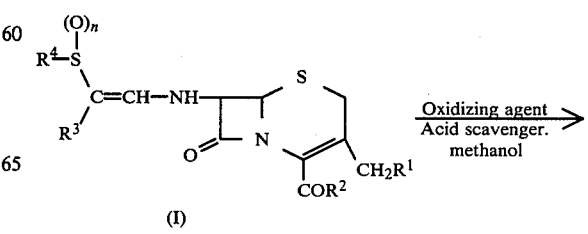

-continued

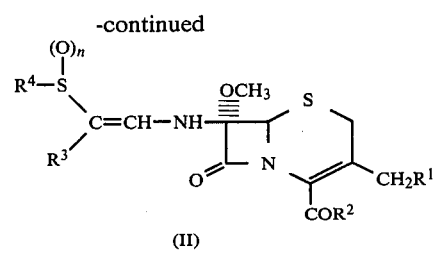

(II)

In the above formulae, $R^1$ represents a hydrogen atom or the group —A—B wherein A is an oxygen atom or a sulfur atom and B is an acyl group; a substituted or unsubstituted heterocyclic group containing as a hetero atom at least one selected from the group consisting of an oxygen atom, a nitrogen atom and a sulfur atom; or a substituted or unsubstituted carbamoyl group: $R^2$ represents a hydroxy group or a carboxyl-protecting group: $R^3$ represents a hydrogen atom, an alkyl group, a substituted or unsubstituted phenyl group or a halogen atom: $R^4$ represents an alkyl group or a substituted or unsubstituted phenyl group: and n is an integer of 1–2.

As the acyl group that is one embodiment of B in $R^1$, there may be mentioned an acetyl group, an acetoacetyl group and the like, while, as the substituent that the heterocyclic group of another embodiment for B may optionally have, there may be mentioned, for example, a lower alkyl group, an aminoalkyl group, a carboxyalkyl group, a sulfoalkyl group and the like. Illustrative examples of such heterocyclic group may include, for example, a 1H-tetrazol-5-yl group, a 1-methyltetrazol-5-yl group, a 1-carboxymethyl-1H-tetrazol-5-yl group, a 2-carboxymethyl-1H-triazol-5-yl group, a 1-sulfoethyl-1H-tetrazol-5-yl group, a 2-carboxymethyl-1-methyl-1H-triazol-5-yl group, a 4-methyl-5-oxo-6-hydroxy-4,5-dihydro-1,2,4-triazin-3-yl group, a pyridinium methyl group, a thiazolyl group, a thiadiazolyl group and the like. As the substituted carbamoyl group, there may be mentioned, for example, a mono-substituted or di-substituted carbamoyl group with e.g., an alkyl group.

$R^2$ is, as defined above, a hydroxy group or a carboxyl-protecting group. As the carboxyl-protecting group, there may be mentioned any protecting group commonly employed in penicillin and cephalosporin fields; for example, a benzhydryloxy group, a tert-butoxy group, a p-nitrobenzyloxy group, a 2,2,2-trichloroethoxy group, a methoxymethoxy group and the like.

As the alkyl group in $R^3$ or $R^4$, there may be mentioned a methyl group, an ethyl group, an isopropyl group, a butyl group, an isobutyl group, a hexyl group, a heptyl group and the like. As the substituted phenyl group, there may be mentioned o-, m- and p-chlorophenyl groups, o-, m- and p-methoxyphenyl groups, o-, m- and p-nitrophenyl groups, o-, m- and p-tolyl groups and so on. As the halogen atom, there may be mentioned chlorine, bromine and the like.

More specifically, according to this invention, there can be provided a new process wherein the compound (II), the new 7α-methoxycephem compound, i.e., the present important end product, can be synthesized by subjecting the compound (I) to the action of an oxidizing agent in the presence of methanol and an acid scavenger (i.e., acid binding agent) or by reacting the compound (I) with an oxidizing agent and subjecting to the action of an acid scavenger in the presence of methanol.

DETAILED DESCRIPTION OF PRFERRED EMBODIMENTS

The reaction from the compound (I) to the compound (II) may be effected in methanol or an organic solvent containing methanol at the room temperature or lower. However, the reaction temperature may be optionally selected upon the types of the acid scavenger and oxidizing agent employed. As the oxidizing agent which may be employed, there may be mentioned, for example, N-bromosuccinimide, N-bromophthalimide, N-bromoacetamide, N-chlorosuccinimide, N-chlorophthalimide, N-chloroacetamide, tert-butyl hypochlorite, methyl hypochlorite, bromine, chlorine and the like and N-bromosuccinimide is preferably used. As the acid scavenger, there may be mentioned, for example, a basic inorganic salt such as borax, potassium carbonate, sodium carbonate and the like; a solid acid scavenger such as silica gel, alumina, molecular sieves, a basic resin and the like; a metal alkoxide such as lithium methoxide, potassium tert-butoxide and the like; an alkali or alkaline earth metal hydroxide; an alkali or alkaline earth metal oxide; a metal amide such as lithium diisopropylamide and the like; an alkali metal hydride such as sodium hydride and the like; an alkyl metal such as an alkyl lithium and the like; a tertiary amine such as triethylamine, diazabicyclononene (DBN), diazabicycloundecene, diisopropylethylamine, pyridine and the like and borax, potassium carbonate, lithium methoxide and alumina are preferably employed.

The oxidizing agent may be usually employed at one equivalent to the compound (I), while the acid scavenger is employed at least at one equivalent, usually 2–3 equivalents to the compound (I).

The present reaction has favourable characteristics that the use of a strong base is not always required, an oxidizing agent may be employed under mild conditions without cleavage of cephem nucleus, there is no need to use such reaction conditions and reagents to cause isomerization easily and so on. Moreover, the present reaction can provide highly efficient 7α-methoxylation with easy recovery of the final product.

Further, the compound (II) of this invention is useful, in particular, as a synthetic intermediate for 7α-methoxycephalosporin derivatives, because the aldehyde moiety (side chain portion) can be very easily eliminated from the compound (II) as illustrated below.

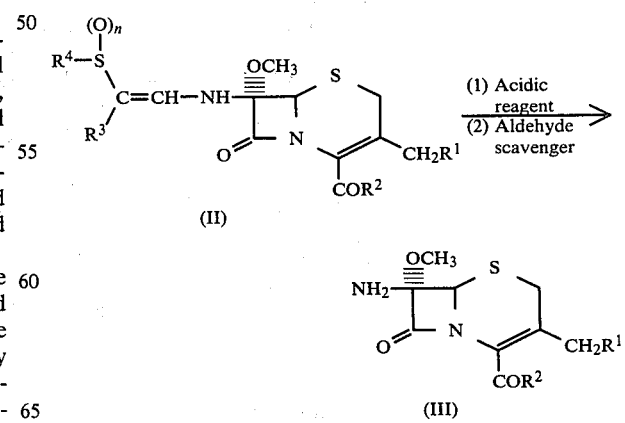

In the above formulae, $R^1$–$R^4$ and n are as defined above. More specifically, the compound (II) may be very easily converted to the 7β-amino-7α-methoxycephem compound (III) by treatment with an acidic reagent and subsequent treatment with, for instance, an aldehyde or ketone binding agent such as various substituted hydrazine derivatives, especially Girard's reagent ("Reagent for Organic Synthesis", p 410, Fieser & Fieser, 1967). As the acidic reagent which may be employed, there may be mentioned an inorganic acid halide such as phosphorus pentachloride, phosphorus oxychloride, phosphorus pentabromide, thionyl chloride, tin chloride, phosphorus trichloride, phosphorus tribromide; an organic acid halide such as acetyl chloride, methanesulfonyl chloride, trifluoromethanesulfonyl chloride, benzoyl chloride; an acid anhydride such as acetic anhydride, trifluoroacetic anhydride, trifluoromethanesulfonic anhydride.

The compound (III) thus prepared may be converted to the 7β-haloacetylamino-7α-methoxycephem compound of the following formula (V) by the action of a haloacetyl halide of the following formula (IV) in a manner known per se, as illustrated below.

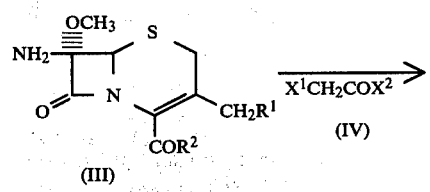

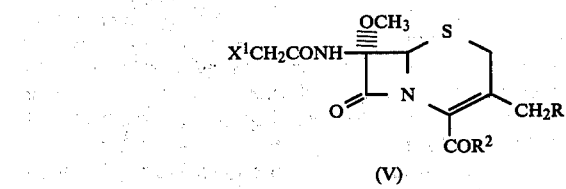

In the above formulae, $R^1$ and $R^2$ are as defined above and $X^1$ and $X^2$ may be the same or different and each represents a halogen atom. The compounds (III) and (V) are generically well-known in the art. For instance, the compound (III) may be converted to the valuable 7α-methoxycephalosporin antibiotic substance, i.e., 7β-(cyanomethylthioacetamido)-7α-methoxy-3-[(1-methyl-1H-tetrazol-5-yl)thiomethyl]-3-cephem-4-carboxylic acid according to the well-known method (The Journal of Antibiotics, 29, 554 (1976)). Also, the compound (V) wherein $X^1=Br$, $R^1=$

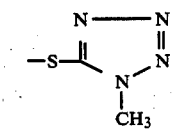

and $R^2=$—O—CH(C$_6$H$_5$)$_2$ may be converted to the valuable 7α-methoxycephalosporin antibiotic substance, i.e., 7β-[(2(R)-2-amino-2-carboxyethyl)thio]acetamido-7α-methoxy-3-[(1-methyl-1H-tetrazol-5-yl)thiomethyl]-3-cephem-4-carboxylic acid according to the well-known method (Japanese Patent Laid-Open Application No. 83791/1980).

The starting material (I) in the present process may be synthesized according to the following reaction schema.

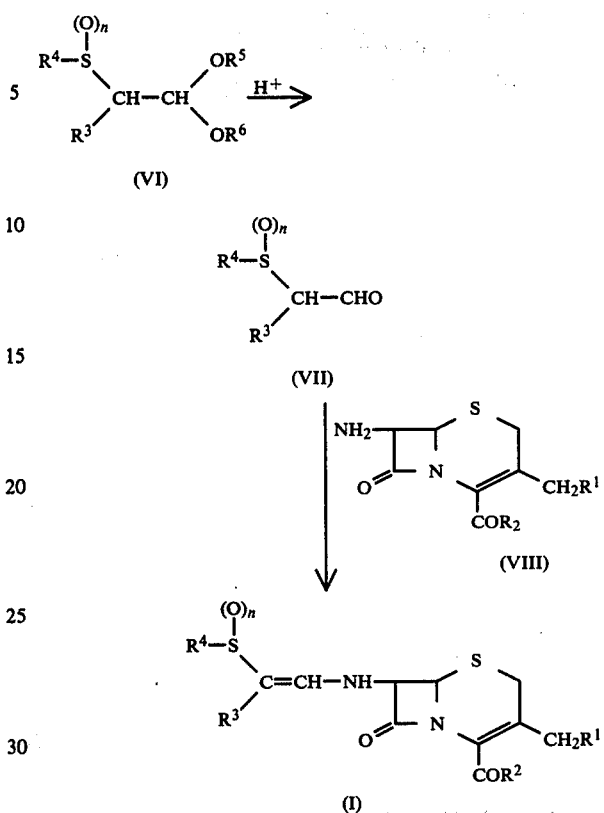

In the above formulae, $R^1$–$R^4$ and n are as defined above and $R^5$ and $R^6$ may be the same or different and each represents a lower alkyl group. More specifically, the compound (VI) wherein n=0 (Yakugaku Zasshi, 71, 546 (1950): Monatsh. Chem., 91, 1070 (1960) is oxidized to the compound (VI) wherein n=1 or 2 and the latter is treated with acid to aldehyde (VII), which is then reacted with 7-aminocephem compound (VIII) to produce the compound (I).

In the above-mentioned steps, the respective intermediates may be isolated and next reaction may be effected. But, as the case may be, suitable several steps may be conducted in a continuous manner without intentional isolation of intermediates.

This invention will be more fully illustrated by way of the following Examples, but these examples are given only for illustration and not construed to be limiting the scope of this invention.

EXAMPLE 1

Benzhydryl 7β-(2-benzenesulfinyl-1-propenylamino)-7α-methoxy-3-(1-methyl-1H-tetrazol-5-yl)thiomethyl-3-cephem-4-carboxylate

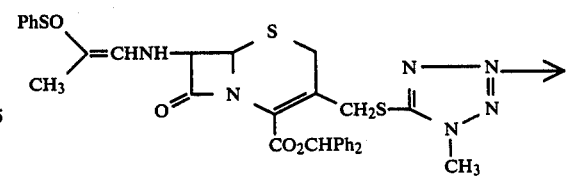

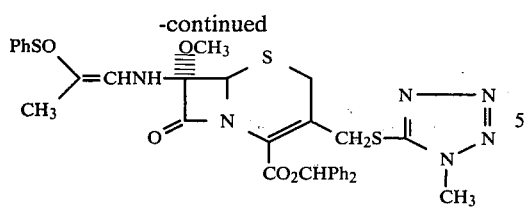

Benzhydryl 7β-(2-benzenesulfinyl-1-propenylamino)-3-(1-methyl-1H-tetrazol-5-yl)thiomethyl-3-cephem-4-carboxylate (1286 mg) was dissolved in a mixture of dichloromethane (20 ml) and methanol (20 ml), borax (1 g) was added to the resulting solution and then the resulting mixture was cooled to −15° C. N-bromosuccinimide (300 mg) was added thereto. The resulting mixture was stirred at −15° C. for 30 minutes and then at room temperature for further one hour. To the reaction mixture was added water and the resulting mixture was extracted with ethyl acetate. The extract was washed with water and dried over magnesium sulfate. The ethyl acetate was distilled off under reduced pressure and the residue was chromatographed with a column of 150 g of silica gel. Elution with toluene: ethyl acetate (1:2) gave 935 mg (69.5%) of the desired product.

PMR (CDCl₃) δ ppm: 1.51 (3H, s), 350 (3H, s), 3.59 (2H, s), 3.80 (3H, s), 4.23 (1H, d, J=14 Hz), 4.53 (1H, s, J=14 Hz), 4.90 (1H, s), 5.23 (1H, d, J=14 Hz), 6.90 (1H, s), 7.0–7.7 (Aromatic H).

EXAMPLE 2

Benzhydryl 7β-(2-p-nitrobenzenesulfinyl-1-propenylamino)-7α-methoxy-3-(1-methyl-1H-tetrazol-5-yl)thiomethyl-3-cephem-4-carboxylate

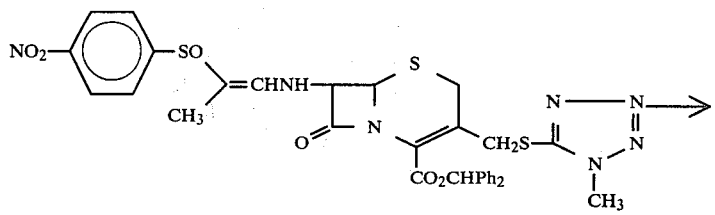

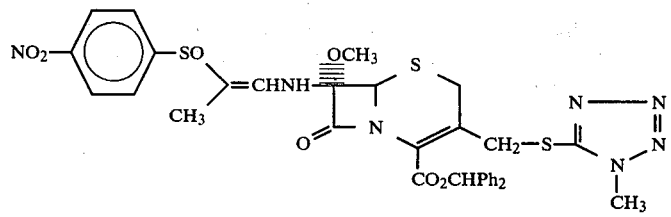

Benzhydryl 7β-(2-p-nitrobenzenesulfinyl-1-propenylamino)-3-(1-methyl-1H-tetrazol-5-yl)thiomethyl-3-cephem-4-carboxylate (352 mg) was suspended in a mixture of dichloromethane (10 ml) and methanol (10 ml). To the resulting suspension was added borax (250 mg) and then N-bromosuccinimide (82 mg) at −15° C. The resulting mixture was stirred at −15° C. for 10 minutes and then at room temperature for further one hour. To the reaction mixture was added water and the resulting mixture was extracted with dichloromethane. The extract was washed with water and dried over magnesium sulfate. The dichloromethane was distilled off under reduced pressure and the residue was chromatographed over silica gel (40 g). Elution with toluene:ethyl acetate (1:1) gave 266 mg (72%) of the desired product.

PMR (CDCl₃) δ ppm: 1.50 (3H, s), 3.56 (3H, s), 3.69 (2H, s), 3.83 (3H, s), 4.25 (1H, d, J=14 Hz), 4.56 (1H, d, J=14 Hz), 4.96 (1H, s), 5.40 (1H, d, J=12 Hz), 6.95 (1H, s), 7.2–7.6 (Aromatic H), 7.78 (2H, d, J=6 Hz), 8.30 (2H, d, J=9 Hz).

EXAMPLE 3

Benzhydryl 7β-[(2-bromo-2-p-nitrobenzenesulfinyl)vinylamino]-7α-methoxy-3-(1-methyl-1H-tetrazol-5-yl)thiomethyl-3-cephem-4-carboxylate

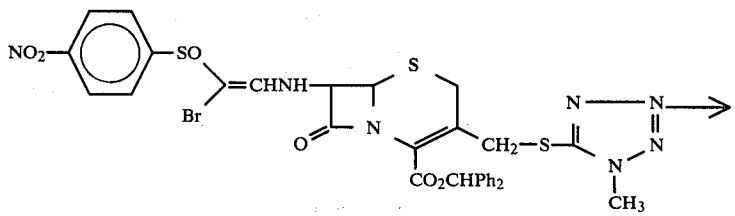

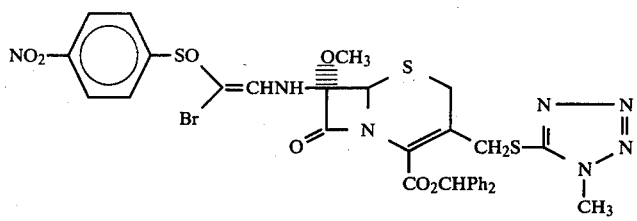

Benzhydryl 7β-[(2-bromo-2-p-nitrobenzenesulfinyl)-vinylamino]-3-(1-methyl-1H-tetrazol-5-yl)thiometyl-3-cephem-4-carboxylate (202 mg) was dissolved in dichloromethane (6 ml) and N-bromosuccinimide (46 mg) was then added to the resulting solution at −15° C. The resulting mixture was stirred at −15° C. for 20 minutes. Thereafter, an aqueous solution of sodium thiosulfate was added to the reaction mixture. The mixture was extracted with dichloromethane. The extract was washed with water, dried over magnesium sulfate and the dichloromethane was distilled off under reduced pressure. The residue was dissolved in a mixture of dichloromethane (5 ml) and methanol (5 ml) and borax (125 mg) was then added thereto. The resulting mixture was stirred at −10° C. for 20 minutes and then at room temperature for further 30 minutes. After addition of water, the reaction mixture was extracted with dichloromethane, the extract was washed with water and dried over magnesium sulfate and then the dichloromethane was distilled off. The residue was column-chromatographed over silica gel (20 g). Elution with toluene:ethyl acetate (4:3) gave 130 mg (62%) of the desired product.

PMR (CDCl₃) δ ppm: 3.48 (3H, s), 3.52 (2H), 4.23 (1H, d, J=14 Hz), 4.57 (1H, d, J=14 Hz), 4.95 (1H, s), 6.02 (1H, d, J=12 Hz), 6.90 (1H, s), 7.2–7.6 (10H, Aromatic H), 7.72 (2H, d, J=9 Hz), 7.76 (1H, d, J=12 Hz), 8.30 (2H, d, J=9 Hz).

EXAMPLE 4

Tert-butyl 7β-[(2-bromo-2-p-nitrobenzenesulfinyl)vinylamino]-7α-methoxy-3-methyl-3-cephem-4-carboxylate

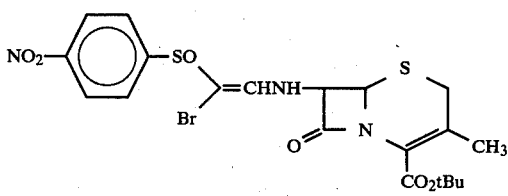

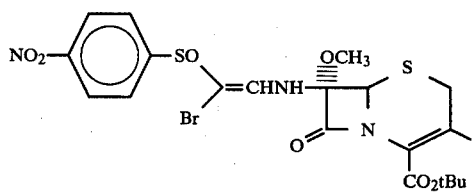

Tert-butyl 7β-[(2-bromo-2-p-nitrobenzenesulfinyl)-vinylamino]-3-methyl-3-cephem-4-carboxylate (55 mg) was dissolved in dichloromethane (2 ml) and N-bromosuccinimide (16 mg) was then added thereto at −17° C. The resulting mixture was stirred at −17° C. for 10 minutes. After addition of an aqueous solution of sodium thiosulfate, the resulting mixture was extracted with ethyl acetate, the extract was washed with water and dried over magnesium sulfate and then the ethyl acetate was distilled off under reduced pressure. The residue was dissolved in a mixture of dichloromethane (2 ml) and methanol (2 ml) and borax (50 mg) was then added thereto. The resulting mixture was stirred at room temperature for 20 minutes. After addition of water, the reaction mixture was extracted with ethyl acetate, the extract was washed with water and dried over magnesium sulfate and then the ethyl acetate was distilled off under reduced pressure. The residue was column-chromatographed over silica gel (5 g). Elution with dichloromethane:ethyl acetate (5:1) gave 37 mg (63%) of the desired product.

PMR (CDCl₃) δ ppm: 1.55 (9H, s), 2.21 (3H, s), 3.18 (2H, Broad s), 3.55 (3H, s), 4.98 (1H, s), 6.03 (1H, d, J=14 Hz), 7.78 (1H, d, J=14 Hz), 7.76 (2H, d, J=9 Hz), 8.33 (2H, d, J=9 Hz).

EXAMPLE 5

Benzhydryl 7β-(2-benzenesulfonyl-1-propenylamino)-7α-methoxy-3-(1-methyl-1H-tetrazol-5-yl)thiomethyl-3-cephem-4-carboxylate

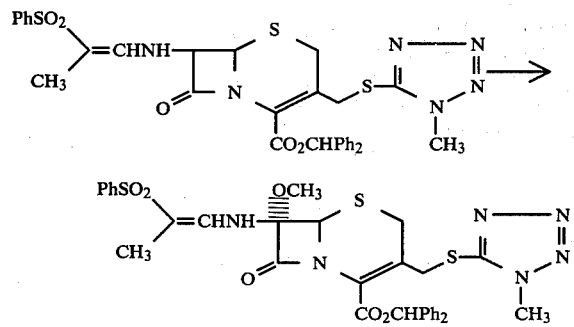

Benzhydryl 7β-(2-benzenesulfonyl-1-propenylamino)-3-(1-methyl-1H-tetrazol-5-yl)thiomethyl-3-cephem-4-carboxylate (753 mg, containing 1 molar ratio of ethyl ether) was dissolved in dichloromethane (10 ml) of N-bromosuccinimide (160 mg) was then added thereto. The resulting mixture was then stirred for 40 minutes at −18° C., and after 25 minutes, further 10 mg of N-bromosuccinimide were added, and methanol (10 ml) and borax (571 mg) were successively added thereto. The resulting mixture was stirred at 0° C. for 45 minutes and then at room temperature for further one hour. After addition of an aqueous solution of sodium chloride, the reaction mixture was extracted with dichloromethane, the extract was dried over magnesium sulfate and then the dichloromethane was distilled off. A small amount of ethyl acetate was added to the residue to separate a crystalline substance, which was then recovered by filtration and dried to yield 450 mg (64%) of the desired product.

PMR (CDCl₃) δ ppm: 1.70, 1.71 (3H), 3.48 (1H, d, J=12 Hz), 3.50 (3H, s), 3.67 (1H, d, J=12 Hz), 3.81 (3H, s), 4.90 (1H, s), 5.03 (1H, d), 6.88 (1H, s), 7.2–7.9 (m).

EXAMPLE 6

Tert-butyl 7β-(2-ethylsulfinyl-1-propenylamino)-7α-methoxy-3-methyl-3-cephem-4-carboxylate

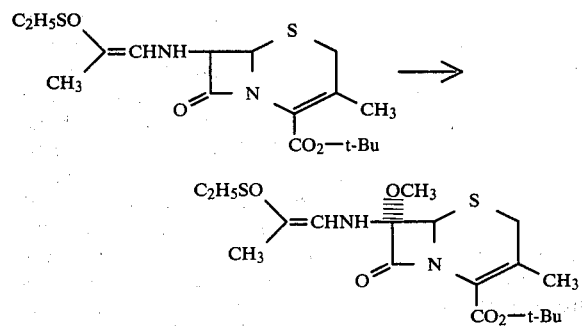

Tert-butyl 7β-(2-ethylsulfinyl-1-propenylamino)-3-methyl-3-cephem-4-carboxylate (111 mg) was dissolved in dichloromethane (2 ml) and N-bromosuccinimide (48 mg) was added thereto. The resulting mixture was stirred at −15° C. for 30 minutes. Then, methanol (4 ml) and borax (171 mg) were added thereto. The resulting mixture was stirred at 0° C. for 30 minutes and then at room temperature for further one hour. After addition of an aqueous solution of sodium chloride, the reaction mixture was extracted with dichloromethane, the extract was dried over magnesium sulfate and the dichloromethane was then distilled off. The residue was column-chromatographed over silica gel. Elution with chloroform:methanol (20:1) gave 63 mg (52.5%) of the desired product.

PMR (CDCl₃) δ ppm: 1.12 (3H, t, J=7 Hz), 1.54 (9H, s), 1.84 (3H, s), 2.12 (3H, s), 2.55–3.08 (2H, m), 3.23–3.36 (2H), 3.51 (3H, s), 4.89 (1H, s), 5.26 (1H, d, J=12 Hz), 6.82 (1H, d, J=12 Hz).

EXAMPLE 7

Tert-butyl 7β-(2-benzenesulfinyl-1-propenylamino)-7α-methoxy-3-acetoxymethyl-3-cephem-4-carboxylate

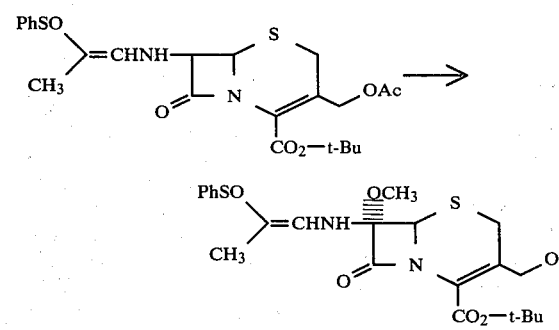

Tert-butyl 7β-(2-benzenesulfinyl-1-propenylamino)-3-acetoxymethyl-3-cephem-4-carboxylate (492 mg) was dissolved in dichloromethane (10 ml) and N-bromosuccinimide (160 mg) was added thereto. The resulting mixture was stirred at −15° C. for 30 minutes. Then, methanol (10 ml) and borax (571 mg) were added thereto. The resulting mixture was stirred at 0° C. for 30 minutes and then at room temperature for further one hour. After addition of an aqueous solution of sodium chloride, the reaction mixture was extracted with dichloromethane, the extract was dried over magnesium sulfate and then the dichloromethane was distilled off. The residue was chromatographed over silica gel. Elution with toluene:ethyl acetate (1:2) gave 380 mg (72.8%) of the desired product.

PMR (CDCl₃) δ ppm: 1.55 (9H, s), 2.08 (3H, s), 3.25 (1H, d, J=18 Hz), 3.64 (1H, d, J=18 Hz), 3.55 (3H, s), 4.81 (1H, d, J=13 Hz), 4.93 (1H, s), 5.15 (1H, d, J=13 Hz), 5.25 (1H, d, J=12 Hz), 7.16 (1H, d, J=12 Hz), 7.4–7.8 (5H, m).

SYNTHESIS EXAMPLE 1

Benzhydryl 7β-(2-benzenesulfinyl-1-propenylamino)-3-(1-methyl-1H-tetrazol-5-yl)thiomethyl-3-cephem-4-carboxylate

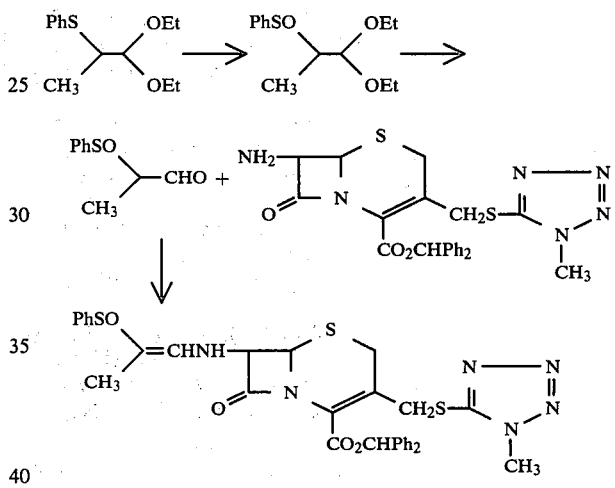

2-Phenylthiopropionaldehyde diethyl acetal (5.6 g) was dissolved in dichloromethane (50 ml) and m-chloroperbenzoic acid (5.3 g) was added thereto under ice-cooling. The resulting mixture was stirred for 2 hours. Then, the reaction mixture was concentrated under reduced pressure, an aqueous solution of sodium hydrogen carbonate was added to the residue and the resultant mixture was then extracted with ether. The extract was washed successively with an aqueous solution of sodium hydrogencarbonate and water, dried over magnesium sulfate and the ether was distilled off under reduced pressure. In acetonitrile (10 ml) was dissolved 1 g of the crude product of 2-benzenesulfinyl-propionaldehyde diethyl acetal thus obtained and the resulting solution was stirred with conc. hydrochloric acid (5 ml) under ice-cooling for 20 minutes. After addition of a saturated aqueous solution of sodium chloride, the resulting mixture was extracted with ethyl acetate, the extract was washed with an aqueous solution of sodium hydrogencarbonate and dried over magnesium sulfate and then the ethyl acetate was distilled off under reduced pressure. The 2-benzenesulfinylpropionaldehyde thus obtained was dissolved in ethanol (3 ml) and benzene (30 ml) was then added thereto. To the resultant solution were added benzhydryl 7β-amino-3-(1-methyl-1H-tetrazol-5-yl)thiomethyl-3-cephem-4-carboxylate (750 mg) and magnesium sulfate (2 g) and the resulting mixture was then stirred at room temperature for one hour. Insolubles were filtered off and the mother liquor was concentrated under reduced pressure. The residue was column-chromatographed over silica gel (80 g) to give 787 mg (79%) of the desired product.

PMR (CDCl$_3$) δ ppm: 1.47 (3H, s), 3.82 (2H, s), 3.88 (3H, s), 4.22 (1H, d, J=14 Hz), 4.53 (1H, d, J=14 Hz), 4.8–5.4 (3H, m), 6.92 (1H, d, J=13 Hz), 7.03 (1H, s), 7.3–7.8 (m, Aromatic H).

SYNTHESIS EXAMPLE 2

Benzhydryl 7β-(bromoacetylamino)-7α-methoxy-3-(1-methyl-1H-tetrazol-5-yl)thiomethyl-3-cephem-4-carboxylate

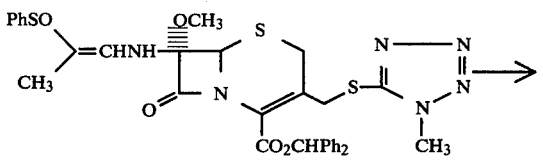

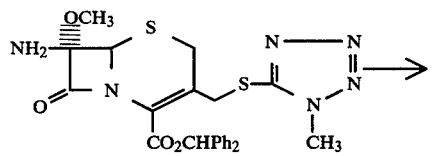

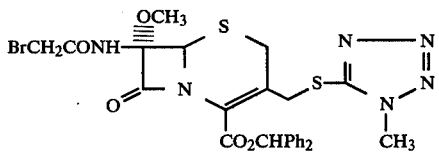

Benzhydryl 7β-(2-benzenesulfinyl-1-propenylamino)-7α-methoxy-3-(1-methyl-1H-tetrazol-5-yl)thiomethyl-3-cephem-4-carboxylate (67 mg) was dissolved in dichloromethane (2 ml) and dimethylaniline (90 mg) was added thereto. To the resulting solution was added phosphorus pentachloride (30 mg) under solid carbon dioxide-hexane cooling and the resulting mixture was stirred under the same temperature as before for 15 minutes. To the mixture were added successively methanol (2 ml) and Girard's reagent T (40 mg). The mixture was then stirred at −10° C. for 2 hours, before the last 15 minutes during that period 20 mg of fresh Girard's reagent T being further added. Thereafter, water was added to the reaction mixture followed by extraction with ethyl acetate. The extract was washed with water, dried over magnesium sulfate and the ethyl acetate solution was then concentrated under reduced pressure to leave an ethyl acetate solution of benzhydryl 7β-amino-7α-methoxy-3-(1-methyl-1H-tetrazol-5-yl)thiomethyl-3-cephem-4-carboxylate.

The solution was cooled to −20° C. and bromoacetyl bromide (0.02 ml) was added thereto. After stirring for 15 minutes, an aqueous solution of sodium hydrogencarbonate was added to the reaction mixture. The resultant mixture was extracted with ethyl acetate, the extract was washed successively with an aqueous solution of potassium hydrogensulfate and water and dried over magnesium sulfate. The ethyl acetate was distilled off under reduced pressure, the residue was column-chromatographed over silica gel (7 g) and elution with toluene:ethyl acetate (2:1) gave 34 mg (52%) of the desired product. The Rf value and PMR of this product were in complete agreement with those of authentic sample.

We claim:

1. A process for preparing a compound of the formula

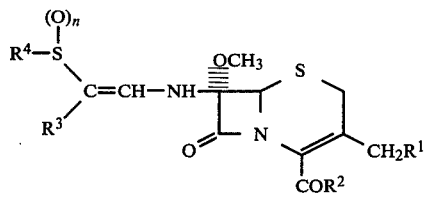

wherein $R^1$ represents a hydrogen atom or the group —A—B wherein A is an oxygen atom or a sulfur atom and B is selected from acetyl, 1H-tetrazol-5-yl, 1-methyl-tetrazol-5-yl, 1-carboxymethyl-1H-tetrazol-5-yl, 2-carboxymethyl-1-methyl-1H-triazol-5-yl, 2-carboxymethyl-1H-triazol-5-yl, 1-sulfoethyl-1H-tetrazol-5-yl or carbamoyl; $R^2$ represents a hydroxy group or a carboxyl-protecting group; $R^3$ represents a hydrogen atom, an alkyl group or a halogen atom; $R^4$ represents an alkyl group or a group selected from phenyl, o-, m- and p-chlorophenyl, o-, m- and p-methoxyphenyl, o-, m- and p-nitrophenyl or o-, m- and p-tolyl; and n is an integer of 1–2, which comprises reacting a compound of the formula

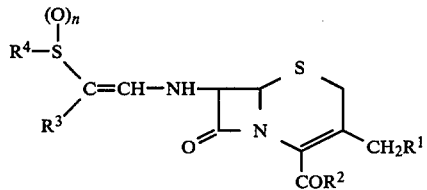

wherein $R^1$, $R^2$, $R^3$, $R^4$, and n are as defined above with an oxidizing agent simultaneously with or subsequently subjecting to the action of methanol and borex.

2. The process according to claim 1 wherein said oxidizing agent is N-bromosuccinimide, N-bromophthalimide, N-bromoacetamide, N-chlorosuccinimide, N-chlorophthalimide, N-chloroacetamide or tert-butyl hypochlorite.

3. The process according to claim 1 wherein said oxidizing agent is N-bromosuccinimide.

* * * * *